United States Patent [19]
Bekki et al.

[11] Patent Number: 5,092,898
[45] Date of Patent: Mar. 3, 1992

[54] ARTIFICIAL JOINT

[75] Inventors: Katsutoshi Bekki; Kiyoshi Shinjo, both of Aichi, Japan

[73] Assignee: NGK Spark Plug Co., Ltd., Aichi, Japan

[21] Appl. No.: 359,171

[22] Filed: May 31, 1989

[30] Foreign Application Priority Data

May 31, 1988 [JP] Japan ............................ 63-132957
Jul. 18, 1988 [JP] Japan ........................ 63-94896[U]

[51] Int. Cl.⁵ ........................................ A61F 2/34
[52] U.S. Cl. ........................................... 623/22
[58] Field of Search ................................ 623/22

[56] References Cited

U.S. PATENT DOCUMENTS 4,842,605 6/1989 Sonnerat et al. ................ 623/22

FOREIGN PATENT DOCUMENTS 2024583 11/1970 Fed. Rep. of Germany.
2261743 9/1975 France ............................ 623/22
2357235 2/1978 France ............................ 623/22
1527498 10/1978 United Kingdom ............. 623/22

Primary Examiner—David J. Isabella
Attorney, Agent, or Firm—Finnegan, Henderson, Farabow, Garrett, and Dunner

[57] ABSTRACT

An artificial femoral head having outer casing and generally spherical head inserted therein with a plurality of bearings inserted therebetween, permitting rotation with a coefficient of friction substantially equal to that of human cartilage. An artificial hip joint having a cup-shaped socket, capable of either being threaded or cemented into a bone cavity, having a generally spherical head inserted therein, having a plurality of bearings therebetween permitting rotation. Another embodiment of the hip joint includes a slide bearing inserted therebetween in addition to the plurality of bearings, permitting rotation in a range up to 120°.

14 Claims, 3 Drawing Sheets

ARTIFICIAL JOINT

BACKGROUND OF THE INVENTION

1. Field of the Invention

The present invention relates to artificial joints, and more particularly to ball and socket replacement joints for human beings. While the invention is applicable to a wide range of artificial joints, it is especially suitable for and will be described particularly in connection with an artificial femoral head that may be needed for replacement due to various reasons, such as fracture or osteoarthritis of the head or neck of the femur. It will also be described in connection with an artificial hip joint that may be needed for replacement of the roof of the acetabulum and the head of the femur for various reasons, such as fracture of the head of the femur, or osteoarthritis of the roof of the acetabulum.

2. Description of the Related Art

The construction of a conventional artificial femoral head is shown in FIG. 1. The head is of a dual structure consisting of an inner ball 17 and an outer ball 15. A slide bearing 16 made of a resin, such as high-density polyethylene, is fitted between the two balls. The inner ball 17 is fitted into the slide bearing 16 and secured with a fixing ring. Both the inner and outer rings are commonly made of metals such as titanium alloys, stainless steel, and CO-Cr-Mo alloys. Attempts have recently been made to form the inner and outer balls of ceramics, which have been commercialized in some areas. However, the slide bearing is still made of a resin and hence has poor wearing characteristics (i.e., wears rapidly).

In most of the conventional artificial femoral heads having the above-described dual structure, the bearing portion is of a slide type made of a high-density polyethylene, and both the inner and outer balls are made of a metal. However, the resin bearing does not have high wear resistance if the outer surface of the inner metallic ball deteriorates for some reason such as corrosion. As a result the slide bearing will become loose, potentially causing a complication such as bone fracture.

Conventional artificial hip joints as shown in FIGS. 16 and 17 comprise an acetabular socket 21, a slide bearing 38 formed of a high-density polyethylene, and an artificial femoral head 22 which is inserted into the socket so that it contacts the inner surface 35 of the bearing 38. The outer surface of the slide bearing may be coated with a metal reinforcement 36 that will prevent deformation of the bearing. In current commercial products of artificial hip joints, threads are cut in the outer surface of the socket so that the joint can be screwed into place. In a bone cement fixing system, the outer surface of the socket is roughened so as to insure good adhesion to the bone cement.

If the hip joint described above is used in the human body for an extended period, the surface of the femoral head which is typically made of a metal will corrode and its surface become so coarse that the bearing portion will wear to an abnormal extent. Attempts have recently been made to use ceramics in the femoral head, which have been commercialized in some areas. With such ceramic femoral heads, the bearing portion will not wear upon contact with the femoral head. However, during prolonged use, the bearing portion will be deformed by cyclic application of load and if the deformation proceeds further, the femoral head will penetrate the bearing portion, making the artificial hip joint no longer suitable for use.

SUMMARY OF THE INVENTION

The present invention is intended to solve the aforementioned problems of the prior art.

In accordance with one aspect of the present invention, an artificial femoral head of a dual structure is provided, in which the inner surface of a hollow in the human body which is to be contacted by the outer surface of an outer ball is furnished with a slide bearing, having a ball-and-roller bearing fitted between the inner and outer balls. More specifically, a bearing consisting of either a train of rolling balls or a retainer having a train of rolling balls fitted therein is furnished as an intermediate layer between the inner ball and the inner surface of the outer ball. To enable the rotation of the inner ball, a ring is fixed or retained in the opening of the outer ball, thus closing the opening to prevent dislodging of the inner ball, while still permitting rotation thereof. If the artificial femoral head is to be used with the roof of the acetabulum, the bearing which is to contact the outer ball permits sliding with the outer surface of the latter which is inserted directly into the acetabular socket. This slide bearing may be made of a ceramic or metallic material. Suitable ceramic materials are high-strength ceramics such as alumina, zirconia, silicon nitride, the compound Si-Al-O-N sold under the trade name SIALON, and silicon carbide. Suitable metallic materials include stainless steel, titanium alloys, high-carbon superhard steels and high-carbon chrome steels. The outer ball may be made of high-density polyethylene or polymethyl methacrylate (PMMA).

In accordance with another aspect of the present invention, there is provided an artificial hip joint having an acetabular socket which is furnished with a thread portion on the outer side or which is to be fixed by means of bone cement. A hemispherical hollow or concavity is formed in the inner surface of the socket and a femoral head having a hemispherical outer surface is rotatably inserted into the hollow with a ball-and-roller bearing being interposed. The openings at the hemispherical surfaces are closed with a fixing ring in such a way that the femoral head will be able to oscillate. This acetabular socket is of a unitary structure. Alternatively, a two-layered socket may be considered which consists of an outer frame and a bearing portion, with a buffer plate being held between them. A train of rolling balls fitted in a retainer may be disposed between the two hemispherical surfaces. If desired, an artificial hip joint of a dual bearing structure may be provided in which the inner surface of the socket having a thread portion on the outer side is designed as a hemispherical sliding surface, which is in slidable engagement with the outer surface of an outer ball whose hollow cavity has a hemispherical inner surface that serves as the rolling surface for the rolling balls in a retainer when the femoral head is rotatably inserted into said cavity. In each of the cases described above, the socket may be designed as fixable by means of bone cement instead of screwing with the aid of the thread portion formed on its outside surface. A unitary structure socket, the rolling balls and the femoral head may be made of ceramic or metallic materials. The ball retainer may be made of a resin. The two layered socket has an intermediate resin or rubber layer inserted between the ceramic or metallic outer frame and bearing portion to serve as a shock absorber. In the case of the dual bearing system, the outer frame of the socket and the outer ball may be made of a ceramic or metallic material, whereas the slide bearing portion is made of a resin. Illustrative ceramic materials include alumina, zirconia, silicon nitride, the compound Si-Al-O-N sold under the trade name SIALON silicon carbide, and composites of these dissimilar materials. Exemplary metallic materials include titanium alloys, stainless steel, Co-Cr-Mo alloys, and shape-memory alloys. Carbon may also be used. The ball retainer and the fixing ring may effectively be formed of high-density polyethylene, polyacetal or high-density polymethyl methacrylate (PMMA), but metals can also be used. Illustrative combinations of dissimilar materials are that of a ceramic material used for the socket and femoral head and a metal used for the rolling balls, and vice versa. The buffer plate may be made of a high-strength resin such as high-density polyethylene, polymethyl methacrylate or high-hardness nylon, or a chemical-resistant rubber material such as urethane rubber, fluorine rubber or silicone rubber.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a preferred embodiment of the invention and, together with the general description given above and the detailed description of the preferred embodiment given below, serve to explain the principles of the invention.

DESCRIPTION OF THE PREFERRED EMBODIMENT

Reference will now be made in detail to the present preferred embodiment of the invention as illustrated in the accompanying drawings.

Figure 1:
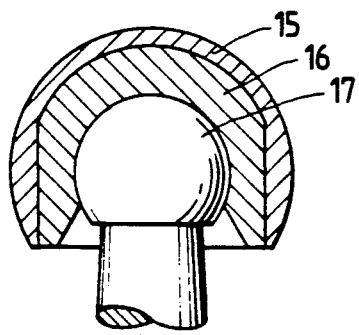
FIG. 1 is a longitudinal sectional view of a conventional artificial femoral head that employs a slide bearing of a dual structure.
Figure 2:
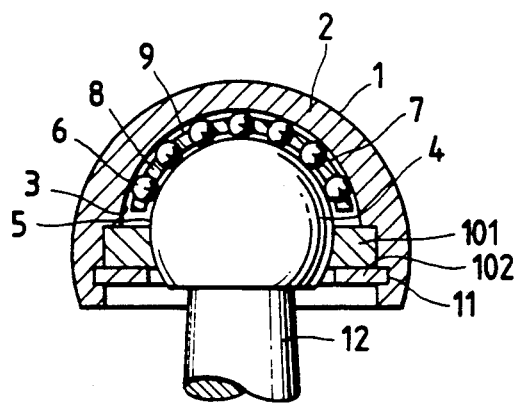
FIG. 2 is a longitudinal sectional view of an artificial femoral head according to the present invention.

FIG. 2 shows an artificial femoral head according to a first embodiment of the present invention. An outer ball 1 is polished to have a mirror finish on both outer and inner surfaces 2 and 3. At the same time, an inner ball 4 is also polished to have a mirror finish on its outer surface 5. A rolling ball 6 is inserted into each of a plurality of holes 7 in a retainer 8 and an end face 9 of each hole is thermally crimped to ensure that none of the rolling balls 6 will be dislodged from the retainer 8. The retainer 8 is then inserted into the outer ball 1 to contact its inner surface 3. Next, the inner ball 4 is fitted in, and a femoral head supporting ring 101 and a fixing ring 102 are fitted into a groove 11 so that the inner ball 4 will not be dislodged from the outer ball 1. The femoral head supporting ring 101 and the inner ball 4 make a spherical pair and are slidable with each other. The femoral head supporting ring is a continuous ring and provides a superior holding property for the inner ball, and further, foreign substances hardly enter the femoral head since the supporting ring and the fixing ring merely have little gaps.

Figure 3:
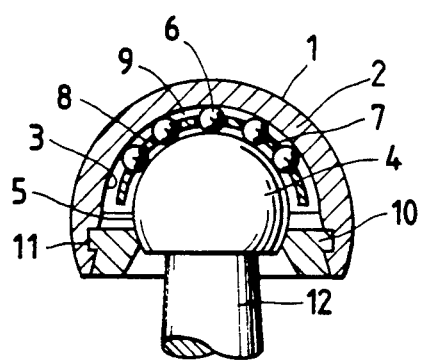
FIG. 3 is a longitudinal sectional view of another artificial femoral head of the present invention.
Figure 4:
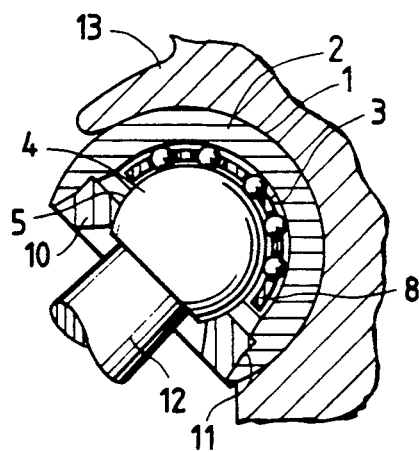
FIG. 4 is a longitudinal sectional view of an artificial femoral head of the present invention inserted into the roof of a human acetabulum.
Figure 5:
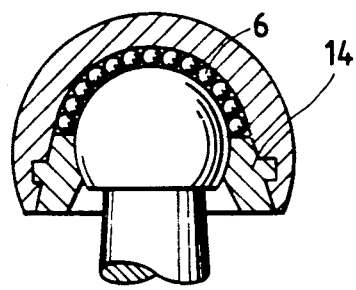
FIG. 5 is a longitudinal sectional view of an artificial femoral head of the present invention having a train of rolling balls fitted between an inner and an outer ball without employing a retainer.

FIG. 3 shows a cross section of another artificial femoral head of the present invention in which a fixing ring 10 not only holds the inner ball but also fixes it to the outer ball. FIG. 4 shows a cross section of an artificial femoral head of the present invention which is inserted into a roof of a human acetabulum 13. FIG. 5 shows a cross-section of another embodiment of the present invention, having a plurality of rolling balls 6, without being fitted in a retainer, provided between an inner and an outer ball, with an opening between the inner and outer balls being closed with a ball mounting ring 14. The retainer 8 may be made of the same ceramic or metallic material as the outer ball. Alternatively, the retainer may be made of a resin such as high-density polyethylene or polyacetal.

In the embodiments described above, the outer ball 1, inner ball 4 and the roller balls 6 are made of a ceramic material such as alumina, zirconia, silicon nitride, the compound Si-Al-O-N sold under the trade name SIALON or silicon carbide. They may also be made of a metal. The retainer 8 and the fixing ring 10 are made of high-density polyethylene but they may also be made of a metal The rolling balls 6 may be made of a dissimilar material from the outer and inner balls 1 and 4 respectively; for example, ceramic inner and outer balls may be combined with metallic rolling balls, or metallic inner and outer balls may be combined with ceramic rolling balls. In the embodiments described above and shown in FIGS. 2-5, the rolling balls are completely spherical but they may be replaced by cylindrical rollers that are fitted in a retainer. Each of the outer ball 1, inner ball 4, and rolling balls 6 may be composed of a metal, whose surface is covered with a ceramic coating. The fixing ring 10 may be made of high-density polyethylene, polyacetal, a metal (inclusive of a shape-memory alloy and the other alloys that are the same as those which are usable as the material of the outer ball), or a ceramic material such as zirconia.

The artificial femoral head of the present invention has a dual structure with a slide bearing furnished between an inner and an outer ball thereof to reduce the coefficient of friction. The ball-and-roller bearing portion of this artificial femoral head has a gap sufficient to ensure good lubrication with the synovial fluid, so that the coefficient of friction becomes substantially equal to that of human articular cartilage, thereby allowing smooth motion of the joint. If the outer and inner balls, as well as the rolling balls are made of a ceramic material, corrosion can be prevented and the mirror finished surfaces of these balls can be maintained over a prolonged period, thus allowing safe use of the artificial femoral head without potential damage to the roof of the human acetabulum.

In everyday life of ordinary people, the hip joint will move most frequently through an angle of 50°-60°. This range of motion may be achieved by a ball-and-roller bearing system. For motions through a larger angle which are less frequent, a slide bearing system is adopted, in which sliding action occurs between the inner surface of the roof of the acetabulum and the outer surface of the outer ball. As a consequence, reduced wear occurs, minimizing development of particles that result from worn parts, thereby reducing the incidence of resultant complications. This result certainly is a benefit to patients. Due to the point where the surfaces of the rolling balls make contact, namely, the outer surface of the inner ball and the inner surface of the outer ball, the surfaces need not necessarily be polished to mirror finish, and there will be no problem in use, as long as complete roundness is insured. This absence of the need to attain mirror finish will lead to a substantial cost reduction.

Figure 6:
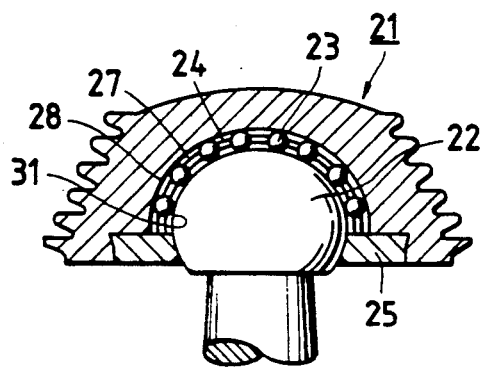
FIG. 6 is a longitudinal sectional view of an artificial hip joint of the present invention having a femoral head inserted oscillatably into a screw-type acetabular socket with a train of rolling balls being fitted in an intervening retainer.

The artificial hip joint of the present invention is described hereinafter with reference to FIGS. 6-15. FIG. 6 is a longitudinal sectional view of an artificial hip joint according to an embodiment of the present invention. A threaded acetabular socket 21 has an arcuate inner surface 31. A plurality of rolling balls 23 fitted in a retainer 24 abutting said inner surface serve as a bearing. A femoral head 22 is inserted rotatably into an opening of socket 21, and the opening is closed with a fixing ring 25 to have the femoral head 22 supported oscillatably. Shown by 27 are holes into which the rolling balls 23 are inserted and 28 shows the area of each hole to be crimped.

Figure 7:
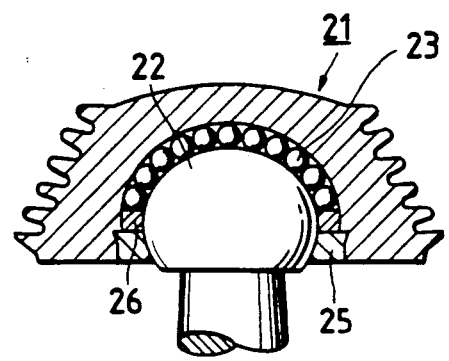
FIG. 7 is a longitudinal sectional view of an artificial hip joint of the present invention having a femoral head inserted into a screw-type acetabular socket with a train of rolling balls being directly interposed.

FIG. 7 shows an artificial hip joint according to another embodiment of the present invention, wherein a plurality of rolling balls 23 are directly inserted (without a retainer) into a threaded acetabular socket 21 so that they contact the inner surface of the socket, and a retaining ring 26 and a fixing ring 25 are mounted to prevent dislodging of the rolling balls.

Figure 8:
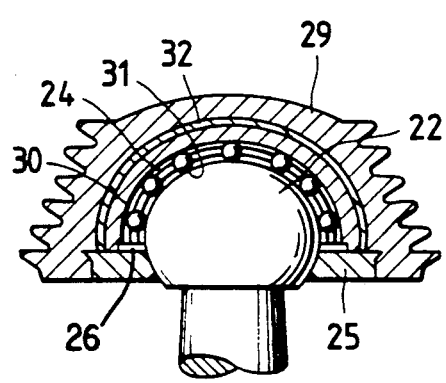
FIG. 8 is a longitudinal sectional view of an artificial hip joint of the present invention having a femoral head inserted into a screw-type acetabular socket of a dual structure and further having an intermediate buffer plate, with a train of rolling balls being fitted in an intervening retainer.

FIG. 8 shows an artificial hip joint in which a screw-type acetabular socket 21 of a split type that consists of an outer frame 29 and a bearing portion 30 furnished with an arcuate inner surface 31 for rolling balls is used, with a buffer plate 32 being provided between the outer frame 29 and bearing portion 30 to make a unitary assembly. A femoral head 22 is inserted into the socket 21 having a retainer 24, with rolling balls 23 interposed therebetween and held in place by means of a fixing ring 25.

Figure 9:
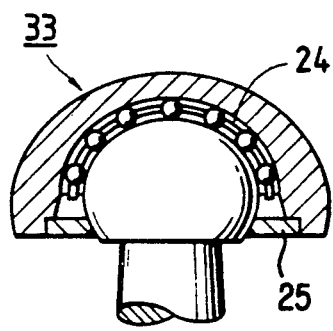
FIGS. 9–11 are cross sectional views of artificial hip joints of FIGS. 6–8, showing a configuration wherein the acetabular socket is to be fixed by means of bone cement instead of screwing.
Figure 10:
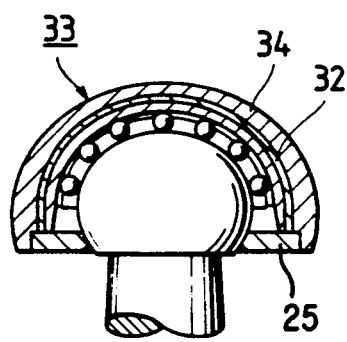
Figure 11:
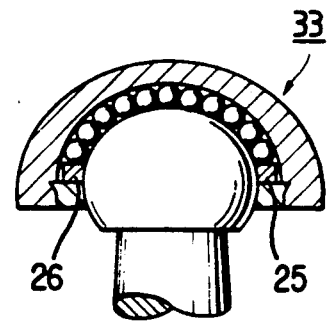

FIGS. 9-11 show artificial hip joint that are the same as those shown in FIGS. 6-8 except that the acetabular socket 21 is fixed to the femoral head by means of bone cement instead of screwing. Referring to FIGS. 9-11, 33 is a cement-fixable acetabular socket, and 34 is an outer frame of the socket.

Figure 12:
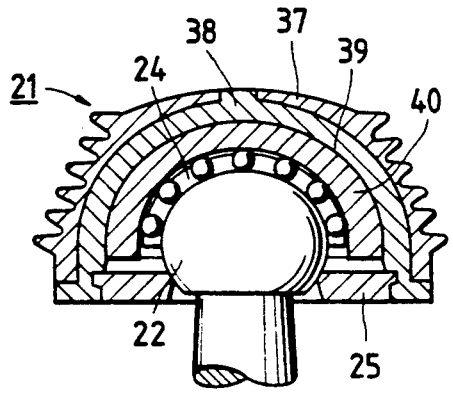
FIG. 12 is a longitudinal view of an artificial hip joint of the present invention wherein an inner surface of a screw-type acetabular socket having a dual bearing structure is formed as a slide bearing surface, which engages an outer ball to cooperate with a ball-and-roller bearing.

FIG. 12 shows another embodiment of an artificial hip joint, in which an acetabular socket 21 is configured to consist of an outer frame 37 and a slide bearing portion 38 on the inside surface thereof, forming a dual bearing system. The inner surface of the bearing portion 38 is formed as an arcuate sliding surface 39, which engages an outer ball of dual bearing type 40 as a rotatable element of a sliding pair. The inner surface of the outer ball 40 is formed arcuate, and as in the embodiment shown in FIG. 6, a femoral head 22 is inserted into the socket 21 together with an intervening retainer 24 having a plurality of rolling balls fitted therein. To insure that the femoral head will be rotatable, the opening between the socket 21 and the femoral head 22 is closed with a fixing ring 25.

Figure 13:
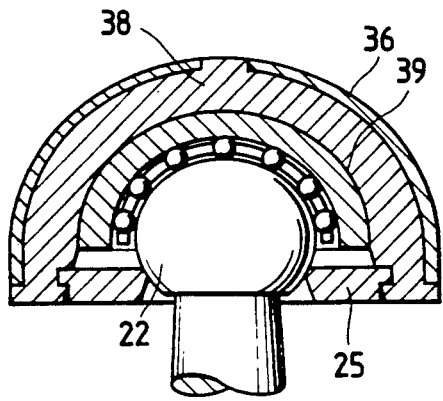
FIG. 13 is a longitudinal sectional view of an artificial hip joint of the present invention having an acetabular socket of a dual bearing structure configured to be fixed by means of bone cement instead of screwing.

FIG. 13 shows an artificial hip joint that is of the same type as shown in FIG. 12 except that the acetabular socket is to be fixed by means of bone cement instead of screwing.

Figure 14:
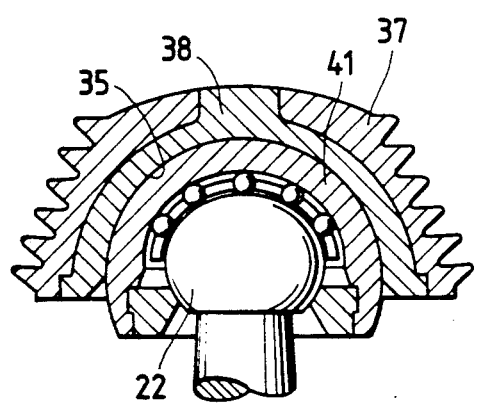
FIG. 14 is a longitudinal sectional view of an artificial hip joint of the present invention wherein the femoral head with rolling balls having a dual structure furnished with an outer ball is inserted rotatably into a conventional screw-type acetabular socket.

FIG. 14 shows an artificial hip joint having a dual ball-and-roller bearing system in which a screw-type acetabular socket is provided with a sliding surface on its inner side, which engages an outer ball 41 on a femoral head 22.

Figure 15:
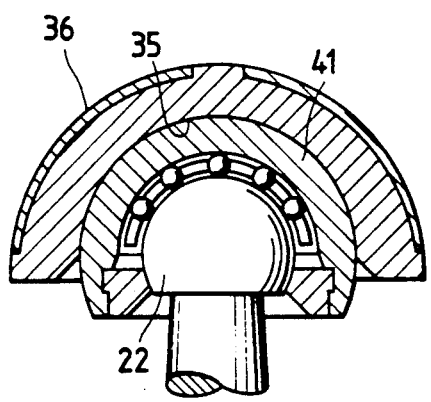
FIG. 15 is a longitudinal sectional view of an artificial hip joint of the present invention wherein the femoral head with rolling balls having a dual structure furnished with an outer ball serving as an element of sliding pair is inserted into a conventional cement fixable acetabular socket.
Figure 16:
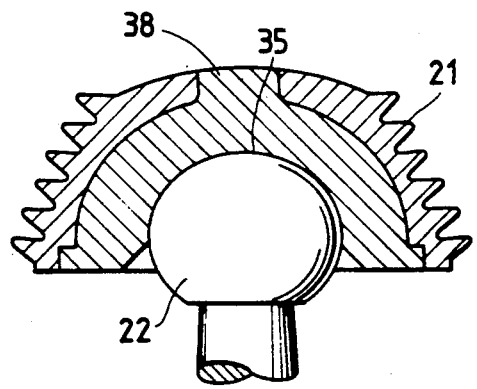
FIG. 16 is a longitudinal sectional view of a conventional artificial hip joint having a screw-type acetabular socket.
Figure 17:
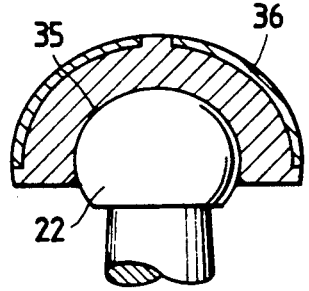
FIG. 17 is a longitudinal sectional view of a conventional artificial hip joint having a cement-fixable acetabular socket.

FIG. 15 shows an artificial hip joint that is of the same type as shown in FIG. 14 except that the acetabular socket is to be fixed by means of bone cement instead of screwing.

The artificial hip joint of the present invention may be implanted in the human hip bone by a method that consists of cutting a thread on the hip bone with a tapping device and then threading the acetabular socket of the joint into the bone. If the acetabular socket has an arcuate outer shape, part of the cavity in the human hip bone is excised and the socket is thereafter pushed into the cavity, followed by fixing it thereto with bone cement.

In the case where the artificial hip joint of the present invention employs an acetabular socket of solid structure, the inner hemispherical surface of the socket is used as a sliding surface over which rolling balls will rotate while at the same time, they roll over the outer surface of the femoral head. In case of an acetabular socket which is composed of two assembled parts, the intermediate buffer plate serves an effective shock absorber. In the case of an acetabular socket of a dual bearing system, the range of everyday hip joint motion which is usually through an angle of 50°-60° is covered by the oscillation of ball-and-roller bearing on the femoral head side. If motion through a larger angle is required, the sliding and oscillating action between the outer ball and the inner surface of the socket combines with the ball-and-roller bearing to expand the range of oscillation to a maximum angle of approximately 120°.

An artificial hip joint according to one embodiment of the present invention which employs an acetabular socket of monolithic structure has the advantage of simple construction and ease of mounting. An artificial hip joint according to another embodiment which employs an acetabular socket of split type having an intermediate buffer plate disposed between the two components has the advantage that impact on the bearing is sufficiently absorbed to prevent failure of the bearing. According to a third embodiment, a hip joint of a dual bearing structure is provided in which a slide bearing is mounted in an acetabular socket furnished with a ball-and-roller bearing. This type of hip joint is capable of a greater range of motion.

The three types of artificial hip joints described above share the feature of adopting a ball-and-roller bearing as the basic system. They exhibit comparatively low coefficients of friction and provide good lubrication with the synovial fluid; the resulting coefficient of friction becomes substantially equal to that of human articular cartilage, thereby allowing smooth motion of the artificial hip joint. If the acetabular socket, femoral head and rolling balls are made of a ceramic material, corrosion can be prevented, thus ensuring prolonged use with consistent results. This would be a great benefit to recipients of artificial hip joints.

Additional advantage and modification will readily occur to those skilled in the art. The invention in its broader aspects is, therefore, not limited to the specific details, representative apparatus and illustrative example shown and described. Accordingly, departures may be made from such details without departing from the spirit or scope of applicants' general inventive concept.

What is claimed is:

1. An artificial femoral head, comprising:
   a casing having an outer surface for attachment to a human bone and a smooth inner arcuate surface having a predetermined diameter defining an opening therein, and a groove formed in the inner surface encircling said opening;
   a generally spherical head member disposed in the opening of the casing, said head member having a smooth outer surface opposing the inner surface of said casing and having a diameter smaller than the predetermined diameter of said casing;
   a plurality of bearing members disposed between the inner surface of the casing and the outer surface of the head member for permitting rotation between the head member and the casing;
   a fixing ring surrounding the opening of said casing mounted between the inner surface of said casing and the outer surface of said head member, said fixing ring having an outer perimeter projecting into the groove formed in the inner surface of the casing, and an inner perimeter adjacent the head member, the inner perimeter having a diameter less than the diameter of said head member, preventing removal of said head member through the opening in said casing; and
   a retaining ring engaging at least a portion of said plurality of bearing members, for retaining said plurality of bearing members between the inner surface of the casing and the outer surface of the head member.

2. The femoral head of claim 1, further including an arcuate retainer element disposed between said casing and said head member, having a plurality of apertures for receiving the bearing members in axial spaced relation to one another.

3. The femoral head of claim 2 wherein said plurality of bearings and retainer element are metallic.

4. The femoral head of claim 2 wherein said plurality of bearings and retainer element are ceramic.

5. The femoral head of claim 1, wherein said plurality of bearings include ball bearings.

6. The femoral head of claim 1, wherein said plurality of bearings include cylindrical roller bearings.

7. The femoral head of claim 1, wherein the outer surface of said casing is threaded for rotatable insertion into the human bone.

8. The femoral head of claim 1, wherein the outer surface of said casing is smooth for attachment to the human bone with bone cement.

9. The femoral head of claim 1, further including an arcuate buffer plate disposed between said inner surface of said socket and said plurality of bearings.

10. The femoral head of claim 1, further including a synovial fluid for lubricating said bearing members.

11. The femoral head of claim 1, wherein said casing is ceramic.

12. The femoral head of claim 1, wherein said head member is ceramic.

13. The femoral head of claim 1, wherein said bearing members are ceramic.

14. The femoral head of claim 1, wherein said bearing members rollingly abut the inner surface of the casing and the outer surface of the head member.

* * * * *